United States Patent [19]

Hobson et al.

[11] Patent Number: 5,147,651
[45] Date of Patent: Sep. 15, 1992

[54] HOOF PACK OF POLYOLEFIN FIBER AND PINE TAR

[76] Inventors: Don R. Hobson, R.D. No. 2, Box 66, Dunkirk, Ind. 47336; Edwin L. Kinney, 1321 Windemere La., Tustin, Calif. 92680

[21] Appl. No.: 512,460

[22] Filed: Apr. 23, 1990

[51] Int. Cl.$^5$ ............ A61K 9/70; A61K 33/18; A61K 47/32; A61L 15/42

[52] U.S. Cl. ............ 424/443; 424/61; 424/407; 424/485; 424/486; 424/196.1; 424/667; 424/670; 424/659; 514/772.4; 514/782; 514/783; 523/111; 523/122; 523/105; 524/78; 524/270; 524/581; 524/582

[58] Field of Search ............ 424/443, 61, 83, 407, 424/485, 486, 196.1; 606/212; 514/782, 783

[56] References Cited

U.S. PATENT DOCUMENTS

| | | | |
|---|---|---|---|
| 81,711 | 9/1868 | Van Wegenen | 424/196.1 |
| 1,067,757 | 7/1913 | Rawson | 424/196.1 |
| 3,118,449 | 1/1964 | Bane | 606/212 |
| 3,927,203 | 12/1975 | Seymour et al. | 424/61 |
| 4,070,451 | 1/1978 | Price | 424/61 |
| 4,663,370 | 5/1987 | Marvel, Sr. et al. | 524/60 |
| 4,822,595 | 4/1989 | Corliss et al. | 424/61 |
| 4,859,694 | 8/1989 | Pavlich | 424/61 |
| 4,996,043 | 2/1991 | Adamich-Saltman | 424/61 |

Primary Examiner—Thurman K. Page
Assistant Examiner—Edward J. Webman
Attorney, Agent, or Firm—Plante Strauss Vanderburgh

[57] ABSTRACT

There is disclosed a composition useful for medicated treatment of hooves of live animals. The composition comprises a major portion of a carrier and hoof penetrant, a minor amount of a filler comprising chiefly polyolefin fibers, and an oil-in-water emulsifier to form a staple composition. The composition can include optional quantities of a medicinal compound. A specific example of the compound comprises approximately 12 weight percent of chopped fibers of a polyolefin such as polyethylene or polypropylene, about 69 percent of a carrier comprising pine tar, paraffin wax and coconut oil, and an oil-in-water emulsifier such as an aliphatic alcohol or alkyl glucose fatty acid ester. Preferably, the composition also includes a medicinal compound such as alcohol, iodine or a soluble iodide. The method comprises packing the hooves of live animals such as horses with the composition. The composition rapidly penetrates the tough, dry and hardened tissues of the hoof, restoring its natural pliability and permitting natural expansion and contraction necessary for the athletic or competition horse.

20 Claims, No Drawings

HOOF PACK OF POLYOLEFIN FIBER AND PINE TAR

BACKGROUND OF THE INVENTION

1. Field of Invention

This invention relates to a composition for treating hooves of live animals, and in particular, to a packing composition for horse's hooves.

2. Brief Statement of the Prior Art

Hooves of live animals, and in particular, horses' hooves must be carefully watched to prevent drying, hardening and toughening of the hoof tissues. When excessive drying or hardening occurs the pliability of the hoof decreases so that the hoof is unable to expand or contract naturally in response to pressures and impacts, such as running and jumping. Various ailments are associated with drying and hardening of a horses's hoof including cracking, flaking, pain and inflammation and infections.

In the past, various ailments resulting from drying and hardening of horses's hooves have been treated with products intended to maintain a desirable level of moisture in the hooves, to stimulate hoof growth or to reduce heat, pain and inflammation.

The difficulty with the various liniments and treating agents that have been used in the prior art is that they can not be readily absorbed by the hoof tissue, particularly the hoof horn along the sole and wall of the hoof. Additionally, these products absorb water, urine, etc., which tend to accelerate contamination or further infection in an affected area. None of the prior treatment agents penetrate rapidly into the tough, dry and hardened tissues of the hoof and none are specifically intended to restore the normal pliability of the hoof to permit natural expansion and contraction.

OBJECTIVES OF THE INVENTION

It is an object of this invention to provide a composition which can be used as a packing compound for horses' hooves.

It is a further object of this invention to provide a packing compound for live animal hooves that includes a penetrant to accelerate penetration of hoof tissue.

It is also an object of this invention to provide a packing composition for horses' hooves that includes medication.

It is an additional object of this invention to provide a method for treating the hooves of live animals by applying to the undersurface of the hooves a packing compound which contains a carrier and hoof penetrant stabilized in a water-repellant composition.

Other and related objectives will be apparent from the following description of the invention.

BRIEF STATEMENT OF THE INVENTION

This invention comprises a composition useful for medicated treatment of hooves of live animals which comprises a major portion of a carrier and hoof penetrant, a minor amount of a filler comprising chiefly polyolefin fibers, and an oil-in-water emulsifier to form a staple composition. The composition can include optional quantities of a medicinal compound. A specific example of the compound comprises approximately 12 weight percent of chopped fibers of a polyolefin such as polyethylene or polypropylene, about 69 percent of a carrier comprising pine tar, paraffin wax and coconut oil, and an oil-in-water emulsifier such as an aliphatic alcohol or alkyl glucose fatty acid ester. Preferably, the composition also includes a medicinal compound such as alcohol, iodine or a soluble iodide. The method comprises packing the hooves of live animals such as horses with the composition. The composition rapidly penetrates the tough, dry and hardened tissues of the hoof, restoring its natural pliability and permitting natural expansion and contraction necessary for the athletic or competition horse.

DESCRIPTION OF PREFERRED EMBODIMENT

This invention comprises a composition useful as a packing compound for the hooves of live animals, particularly for horses' hooves. The composition comprises a homogenous mixture of a carrier and hoof penetrant filled with synthetic fibers such as polypropylene or polyethylene, and an oil-in-water emulsifier.

The synthetic fiber is extruded polyethylene or polypropylene having lengths from about 0.1 to about 2 inches, preferably from about 0.25 to about 1 inch. Various extruded fibrous forms of the polyolefins can be used; tubular extrusions are preferred, however solid-form strands or other fibrous forms can also be employed.

The fiber component is used in the composition in an amount from about 5 to 25 weight percent, preferably from about 7 to about 17 weight percent.

An optional filler, which improves the consistency of the composition is starch, preferably corn starch. The starch, when used, can comprise from about 2 to 10 weight percent, preferably from 4 to about 8 weight percent of the composition.

The composition contains major portion of a carrier containing a hoof penetrant Various tars, preferably plant tars and pitches are used as penetrants and preferred to provide a penetrating characteristic to the composition. A very suitable material is pine tar as this material is very stable and has a high penetration for the tissue of animal hooves.

The carrier containing a hoof penetrant is used in an amount from about 55 to about 80 weight percent, preferably from about 65 to 75 weight percent of the composition. The plant tar comprises 65 to 80 percent of the carrier, and the other additives such as vegetable oils and/or wax, described below, when used comprise 20 to 35 percent of the carrier.

The plant tar can be used with an oil, preferably vegetable oils such as palm oil, coconut oil, and the like. The oils are used to soften the tar and provide a carrier which is more amenable to blending with the emulsifier and fillers.

Another optional additive is a mineral oil paraffin wax. This additive also improves the blending of the carrier with additives, and provides a desirable water resistance to the composition. The wax, when present, is used at a concentration of about 1 to 8, preferably 2 to 6 weight percent of the composition. When a paraffin wax is used together with a vegetable oil, the oil is present in approximately 2 to 3 weight part for each part of wax. The composition is stabilized by use of a suitable oil-in-water emulsifier. Various emulsifiers can be used for this purpose; high molecular weight, aliphatic alcohols, e.g., aliphatic alcohols containing from 12 to about 22 carbons are preferred. Another class of preferred emulsifiers are the alkyl glucose esters of fatty acids, e.g., methyl glucose stearate, methyl glucose sesquistearate, ethylene glucose linoleate, methyl glucose oleate, and the like. The oil-in-water emulsifier is used in an amount from about 1 to about 10 weight percent, preferably from about 2 to 10 weight percent, preferably from 3 to about 7 weight percent of the composition. The emulsifier is used within the aforementioned limits at a concentration sufficient to provide a stable and homogenous mixture of the synthetic fiber and carrier.

The composition also contains, optionally, a suitable medicinal compound. Examples of suitable medicinal compounds tincture of iodine, or the water soluble iodide salts such as potassium iodine. Other topical medicinal agents include isopropanol, hydrogen peroxide, boric acid, etc. The aforementioned medicinal compounds are used at effective medical concentrations which, depending upon the particular medicinal agent, can be from about 0.5 to about 10 weight percent, preferably from about 1 to about 5 weight percent, of the final composition.

Animal hooves have an outer hard shell or horn which surrounds a softer tissue center or undersurface, which has a slight depression. The composition is applied as a packing in this depression or cavity in the undersurface of the hoof. For this purpose, the composition is preferably packaged in the form of individual packs of the composition typically weighing from 0.5 to about 5, preferably from 1.5 to about 2 ounces and having a flat disc-like configuration suitable for placement in the cavities on the undersurface of horses' hooves. The composition has a natural tack and adhesiveness for the hoof tissue permitting it to be used directly without any auxiliary retaining means. It can, however, also be used with bandages, tape, leather, synthetic pads or shoes, all of which can be used to aid its retention on the hoof.

The ingredients of the composition readily penetrate toughened, hardened and dry tissues of the hoof, restoring pliability and permitting natural expansion and contraction of the hoof. The medicinal compounds combat bacterial and fungal infections and the composition forms a moisture repellent barrier or shield against contamination of the hoof by water and urine, thereby further enhancing its fungicidal activity. The components are extremely effective on thrush and abscesses, commonly found in horses hooves. The medications can be packed directly into punctures, cuts and wounds, aiding the healing process and shielding against outside contaminants.

The invention will now be described with reference to the following example which will illustrate the composition and its method of application and demonstrate results obtainable thereby.

EXAMPLE

A packing composition according to the invention is prepared by blending the following ingredients:

| INGREDIENT | WEIGHT PARTS |
|---|---|
| Pine tar: | 52 |
| Coconut Oil: | 13 |
| Paraffin Wax: | 4 |
| Polyethylene Fibers: | 12 |
| Corn Starch: | 6 |
| Surfactant: | 6 |
| Medicinal[1]: | 7 |

[1] a mixture of iodine crystals and potassium iodide in isopropyl alcohol.

The aforementioned ingredients were blended together to prepare a stable homogenous mixture. The mixture was impregnated into cloth pads to prepare packs approximately 2.5 inches in diameter, and 0.5 inch thick. The pads were applied to hooves of horses which exhibited a dry, hardened and tough condition. After 2 days, the pads were removed and the hooves were inspected and it was observed that pliability was restored to the hooves.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

What is claimed is:

1. A composition for treatment of hooves of horses which comprises:
   a. a filler comprising fibers of a polyolefin selected from the group consisting of polypropylene and polyethylene having lengths from about 0.1 to about 2 inches in an amount from 5 to about 25 weight percent of the composition;
   b. a carrier in an amount sufficient to enhance the penetration properties of the composition and from 55 to about 80 weight percent of the composition and comprising a mixture of from 65 to 80 weight percent of a hoof penetrant selected from the group consisting of pine tars and pitches and from 20 to 35 weight percent of an additive selected from the group consisting of vegetable oils and wax;
   c. an oil-in-water emulsifier in an amount from 2 to about 10 weight percent of the composition; and
   d. from 2 to about 10 weight percent starch.

2. The method of treating hooves of live animals which comprises applying to the undersurface of the hooves the packing compound comprising the composition of claim 1.

3. A composition for treatment of hooves of horses which comprises:
   a. a filler comprising fibers of a polyolefin selected from the group consisting of polypropylene and polyethylene having lengths from about 0.1 to about 2 inches in an amount from 5 to about 25 weight percent of the composition;
   b. a carrier in an amount sufficient to enhance the penetration properties of the composition and from 55 to about 80 weight percent of the composition and comprising a mixture of from 65 to 80 weight percent of a hoof penetrant selected from the group consisting of pine tars and pitches and from 20 to 35 weight percent of a mineral oil paraffin wax in an amount from 1 to about 8 weight percent; and
   c. an oil-in-water emulsifier in an amount from 2 to about 10 weight percent of the composition.

4. The method of treating hooves of live animals which comprises applying to the undersurface of the hooves the composition of claim 3.

5. A composition for medicated treatment of hooves of horses which comprises:
   a. a filler comprising fibers of a polyolefin selected from the group consisting of polypropylene and polyethylene having lengths from about 0.1 to about 2 inches in an amount from 5 to about 25 weight percent of the composition;
   b. a carrier in an amount sufficient to enhance the penetration properties of the composition and from 55 to about 80 weight percent of the composition and comprising a mixture of from 65 to 80 weight percent of a hoof penetrant selected from the group consisting of pine tars and pitches and from 20 to 35 weight percent of an additive selected from the group consisting of vegetable oils and wax;

c. an oil-in-water emulsifier in an amount from 2 to about 10 weight percent of the composition; and d. medication in an amount from about 0.1 to about 10 weight percent.

6. The method of treating hooves of live animals which comprises applying to the undersurface of the hooves the composition of claim 5.

7. The composition of claim 5 wherein said medication is iodine or potassium iodide.

8. The method of treating hooves of live animals which comprises applying to the undersurface of the hooves the composition of claim 7.

9. A composition for treatment of hooves of horses which comprises:

a filler comprising fibers of a polyolefin selected from the group consisting of polypropylene and polyethylene having lengths from about 0.1 to about 2 inches in an amount from 5 to about 25 weight percent of the composition;

b. a carrier in an amount sufficient to enhance the penetration properties of the composition and from 55 to about 80 weight percent of the composition and comprising a mixture of from 65 to 80 weight percent of a hoof penetrant selected from the group consisting of pine tars and pitches and from 20 to 35 weight percent of an additive selected from the group consisting of vegetable oils and wax; and c. an oil-in-water emulsifier in an amount from 2 to about 10 weight percent of the composition and comprising an aliphatic alcohol having from 12 to about 22 carbons.

10. The method of treating hooves of live animals which comprises applying to the undersurface of the hooves the composition of claim 9.

11. The composition of claim 9 wherein said alcohol is stearyl alcohol.

12. The method of treating hooves of live animals which comprises applying to the undersurface of the hooves the composition of claim 11.

13. A composition for treatment of hooves of horses which comprises:

a. a filler comprising fibers of a polyolefin selected from the group consisting of polypropylene and polyethylene having lengths from about 0.1 to about 2 inches in an amount from 5 to about 25 weight percent of the composition;

b. a carrier in an amount sufficient to enhance the penetration properties of the composition and from 55 to about 80 weight percent of the composition and comprising a mixture of from 65 to 80 weight percent of a hoof penetrant selected from the group consisting of pine tars and pitches and from 20 to 35 weight percent of an additive selected from the group consisting of vegetable oils and wax; and c. an oil-in-water emulsifier in an amount from 2 to about 10 weight percent of the composition and comprising an alkyl glucose ester of a fatty acid.

14. The method of treating hooves of live animals which comprises applying to the undersurface of the hooves the composition of claim 13.

15. The composition of claim 13 wherein said emulsifier is methyl glucose sesquistearate.

16. The method of treating hooves of live animals which comprises applying to the undersurface of the hooves the composition of claim 15.

17. A composition for treatment of hooves of horses which comprises:

a. a filler comprising fibers of a polyolefin selected from the group consisting of polypropylene and polyethylene having lengths from about 0.1 to about 2 inches in an amount from 5 to about 25 weight percent of the composition;

b. a carrier in an amount sufficient to enhance the penetration properties of the composition and from 55 to about 80 weight percent of the composition and comprising a mixture of from 65 to 80 weight percent of pine tar and from 20 to 35 weight percent of an additive selected from the group consisting of vegetable oils and wax; and c. an oil-in-water emulsifier in an amount from 2 to about 10 weight percent of the composition.

18. The method of treating hooves of live animals which comprises applying to the undersurface of the hooves the composition of claim 17.

19. A composition for treatment of hooves of horses which comprises:

a. a filler comprising fibers of a polyolefin selected from the group consisting of polypropylene and polyethylene having lengths from about 0.1 to about 2 inches in an amount from 5 to about 25 weight percent of the composition;

b. a carrier in an amount sufficient to enhance the penetration properties of the composition and from 55 to about 80 weight percent of the composition and comprising a mixture of from 65 to 80 weight percent of a hoof penetrant selected from the group consisting of pine tars and pitches and from 20 to 35 weight percent coconut oil and c. an oil-in-water emulsifier in an amount from 2 to about 10 weight percent of the composition.

20. The method of treating hooves of live animals which comprises applying to the undersurface of the hooves the composition of claim 19.

* * * * *